United States Patent
Mullen et al.

(10) Patent No.: US 7,016,952 B2
(45) Date of Patent: Mar. 21, 2006

(54) SYSTEM AND METHOD FOR UNIVERSAL REMOTE ACCESS AND DISPLAY OF DIAGNOSTIC IMAGES FOR SERVICE DELIVERY

(75) Inventors: Paul Lawrence Mullen, Waukesha, WI (US); Hubert Anthony Zettel, Waukesha, WI (US)

(73) Assignee: GE Medical Technology Services, Inc., Pewaukee, WI (US)

( * ) Notice: Subject to any disclaimer, the term of this patent is extended or adjusted under 35 U.S.C. 154(b) by 692 days.

(21) Appl. No.: 09/683,611

(22) Filed: Jan. 24, 2002

(65) Prior Publication Data

US 2003/0140141 A1    Jul. 24, 2003

(51) Int. Cl.
*G06F 15/16* (2006.01)
*G06F 15/173* (2006.01)
*G06F 17/60* (2006.01)

(52) U.S. Cl. .................. 709/224; 709/217; 709/218; 709/219; 705/2; 705/3

(58) Field of Classification Search ................ 702/185; 705/2, 3; 725/105
See application file for complete search history.

(56) References Cited

U.S. PATENT DOCUMENTS

| | | | |
|---|---|---|---|
| 6,578,002 B1 * | 6/2003 | Derzay et al. | 705/2 |
| 6,597,473 B1 * | 7/2003 | Rasmussen et al. | 358/1.9 |
| 6,598,011 B1 * | 7/2003 | Howards Koritzinsky et al. | 702/185 |
| 2001/0018659 A1 * | 8/2001 | Koritzinsky et al. | 705/3 |
| 2002/0004798 A1 * | 1/2002 | Babula et al. | 705/2 |
| 2002/0073429 A1 * | 6/2002 | Beane et al. | 725/105 |

* cited by examiner

Primary Examiner—Rupal Dharia
Assistant Examiner—Quang N. Nguyen
(74) Attorney, Agent, or Firm—Ostrager Chong Flaherty & Broitman P.C.

(57) ABSTRACT

Systems and methods for enabling universal remote access and display of diagnostic images acquired by diagnostic imaging equipment, independent of the identity of the vendor that manufactured the equipment. One system includes a local area network; a scanner capable of sending objects formatted in accordance with a communications protocol, each object incorporating at least one image frame; and a data capture device connected to the local area network and programmed with data capture software to capture an object originating from the scanner in response to that scanner being specified as an object of diagnosis. This system further includes a communications channel, e.g., a virtual private network, for connecting the data capture device to a central service facility. The preferred communications protocol is DICOM. In response to an instruction from the service center, the data capture device on the LAN captures image files from a malfunctioning scanner and forwards them to the service center for diagnosis.

15 Claims, 3 Drawing Sheets

SYSTEM AND METHOD FOR UNIVERSAL REMOTE ACCESS AND DISPLAY OF DIAGNOSTIC IMAGES FOR SERVICE DELIVERY

BACKGROUND OF INVENTION

This invention generally relates to imaging systems used in medical diagnostics. In particular, the invention relates to the transfer of digital images from an imaging system over a network to remote devices for archiving, viewing and/or printing.

Modern medical diagnostic imaging systems typically include circuitry for acquiring image data and for transforming the data into a useable form, which is then processed to create a reconstructed image of features of interest within the patient.

The image data acquisition and processing circuitry is referred to as a "scanner", regardless of the modality, if physical or electronic scanning occurs as part of the imaging process. The particular components of the system and related circuitry, of course, differ greatly between modalities due to their different physics and data processing requirements.

Conventional scanners create two-dimensional images of biological tissue by scanning in a scan plane. When the scanner is swept over an area of body, a succession of image frames (corresponding to spaced slices intersecting the body being examined) can be displayed on a monitor. These images can also be stored internally, e.g., on a scanner hard drive or magneto-optical device (MOD).

In addition to storing images internally, modern imaging systems need to be able to transfer images to various types of remote devices via a communications network. To successfully transfer images, the relevant networking features of the scanner must be compatible with the networking features of the destination remote device. In particular, the scanner must place the data to be transferred in a format that can be handled by the destination remote device. An attempt to accomplish the foregoing is the adoption of the DICOM (Digital Imaging and Communications in Medicine) standards, which specify the conformance requirements for the relevant networking features. The DICOM standards are intended for use in communicating medical digital images among printers, workstations, acquisition modules (such as an ultrasound imaging system, a magnetic resonance imaging system, an X-ray machine, or a computerized tomographic scanner), and file servers. The acquisition module is programmed to transfer data in a format that complies with the DICOM standards, while the receiving device is programmed to receive data that has been formatted in compliance with those same DICOM standards.

The DICOM system is designed to facilitate the communication of digital images of different types, e.g., X-ray, computerized tomography, magnetic resonance and ultrasound imaging. For example, in an ultrasound scanner having conventional DICOM capability, three local real-world activities occur: Image Send, Image Print and Remote Verification. Image Send and Image Print can be done in either automatic or manual mode. Verification of remote DICOM devices configured on the ultrasound scanner is performed when the scanner is powered up or when requested by the system operator.

In order to accomplish image transfer, the imaging system must know the configuration of the destination remote device prior to attempting to communicate with that device. The configuration data for the destination remote device is typically inputted to the scanner during software installation by a field engineer, although the DICOM network can be configured at any time. When the scanner receives an instruction to transmit data to a particular remote device from the system operator, the scanner software converts the image data to be transferred into the DICOM format required by the destination remote device, based on the configuration data for that device stored in the imaging system memory. The scanner also sends a request over the network to the destination remote device to open an association, i.e., to connect the scanner to the destination remote device. If the remote device responds in the affirmative, the scanner and remote device then agree on which device will act as the server and which as the client. The scanner also selects the appropriate encoding syntax from those accepted by the remote device. Other communication parameters are also negotiated.

After the DICOM communications protocol has been settled, the association is opened and the scanner attempts to send the DICOM-formatted image file (object) to the remote device via the network. The transfer is done in the background while scanning or other operator activities continue. If the remote device is a storage device, each image file is transferred singly in response to a Send request inputted by the operator. If the remote device is a printer configured to print multi-image film, then a number of images are accumulated to make up a multi-image film and an association is opened in response to a Send instruction when a number of images sufficient to fill the multi-image film have been accumulated.

Medical diagnostic systems of the type described above are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. Moreover, service offerings have been supplemented in recent years by service centers capable of contacting scanners at subscribing institutions directly without the need for intervention on the part of the institution personnel. Such centralized servicing is intended to maintain the diagnostic systems in good operational order without necessitating the attention of physicians or radiologists, and is often quite transparent to the institution.

In certain centralized servicing systems, a computerized service center will contact a scanner via a network to check system configurations and operational states, to collect data for report generation, and to perform other useful service functions. Such contacts can be made periodically, such as during system "sweeps", in which a variety of system performance data is collected and stored with historical data for the particular scanner. The data can then be used to evaluate system performance, propose or schedule visits by service personnel, and the like.

Typically, remote access to diagnose and troubleshoot image quality of diagnostic imaging equipment is restricted to capabilities used by the various OEM device service organizations and is not available to other multi-vendor servicers. For example, in the case where a service provider services diagnostic imaging equipment of its own manufacture, that equipment may be programmed with software that allows the equipment user to request remote support by simply pressing a key or button on the operator console, i.e., user interface. The scanner responds by collecting data that would normally be used by an on-line engineer to diagnose system performance and then sending that data and user/system information in TCP/IP format to a central service facility, where an on-line engineer can use it to provide customer support.

However, the foregoing procedure becomes problematic in the case where a service provider services equipment manufactured by a competitor. In many cases, a service provider may be unable to remotely access equipment manufactured by a competitor. There is a need for a system and method for enabling remote access and review of the acquired image data independent of the particular OEM that manufactured the equipment.

SUMMARY OF INVENTION

The present invention is directed to a system and method for enabling universal remote access and display of diagnostic images acquired by diagnostic imaging equipment, independent of the identity of the vendor that manufactured the equipment.

The method in accordance with one preferred embodiment comprises the step of sending a troubled image, i.e., an image of poor quality, from a malfunctioning scanner to a data capture device via a local area network using an accepted communications protocol. For example, in the case of medical diagnostic images, the accepted communications protocol is preferably DICOM. The troubled image, in DICOM format, is received and stored by the data capture device on the local area network. The data capture device is in turn programmed to notify a central service facility that a troubled image has been received from a particular scanner. Later the troubled image is sent from the data capture device to the central service facility, where a service support engineer can view the troubled image on his/her workstation and try to diagnose the problem inside the malfunctioning scanner. In accordance with this preferred embodiment, the malfunctioning scanner must be configured to communicate with the data capture device, in the same way that the scanner needs to be configured with any remote DICOM-compatible device. This method allows a central service facility to diagnose image quality problems in scanners that the service center is unable to access directly.

In accordance with a second preferred embodiment, the scanner need not be configured to communicate with the data capture device. Instead a scanner user who is experiencing image quality problems on the scanner may notify, e.g., by e-mail, the central service facility of the existence of a problem. The central service facility in turn instructs the data capture device to monitor the local area network and capture all communications that originate from the malfunctioning scanner. In particular, the data capture device uses "sniffing" software to detect any DICOM communications on the LAN having a header that identifies the malfunctioning scanner as the addresser. The data capture device captures the transmitted DICOM files and later sends them to the central service facility for diagnosis of the image quality problem.

Alternatively, the central service facility can monitor DICOM traffic on a local area network without waiting for calls for service from customers. For example, after a scanner has been serviced, the service provider may wish to monitor the image quality on the scanner for a predetermined period of time. This can be done by simply sending to the data capture device the identifier used by the scanner which communicating via the network, with an instruction to capture all images sent onto the network by that scanner.

The data capture device proceeds to monitor DICOM traffic on the network, detecting all transmissions that originated from the identified scanner and capturing those image files. Later the image files are sent to the service center for viewing by a service support engineer.

The system in accordance with one preferred embodiment comprises a local area network; a scanner capable of sending objects formatted in accordance with a communications protocol, each object incorporating at least one image frame; and a DICOM-compatible data capture device connected to the local area network and programmed with software (hereinafter "data capture software") for capturing objects originating from a particular scanner in response to an instruction, received via a communications channel, that specifies the particular scanner as an object of diagnosis. The system further comprises a central service facility connecting to the data capture device via the aforementioned communications channel. After DICOM image files have been captured, the data capture device will send those captured images to the central service facility via the communications channel. Preferably, the communications channel forms part of a virtual private network.

In accordance with a further preferred embodiment, the system comprises a secure web server programmed to download data capture software to a computerized device via a wide area network, e.g., the Internet, in response to receipt of an authorized request. More specifically, the download proceeds only if the web server receives a valid authorization code from the computerized device. The authorized code is inputted by a subscribing customer or by a field engineer. If the download is successful, that customer or field engineer may use the data capture software to monitor traffic and collect specified data, e.g., DICOM objects originating from a specified scanner, on a local area network. The data capture software includes programming for communicating with a central service facility, e.g., via the aforementioned web server.

In accordance with a further aspect of the invention, a preferred method of remotely servicing a scanner from a central service facility comprises the steps of monitoring traffic on a local area network, which traffic is formatted in accordance with a communications protocol; specifying a scanner; capturing from the traffic all data originating from the specified scanner; sending the captured data to the central service facility; and diagnosing a problem associated with the specified scanner using the captured data received at the central service facility. The monitoring, capturing and sending steps are performed by a computerized data capture device connected to the local area network. Preferably, the captured data is sent from the data capture device to the central service facility via a virtual private network. The scanner is specified in a communication sent from the central service facility to the data capture device. The diagnosing step preferably comprises diagnosing an image quality problem afflicting the specified scanner. Preferably, the communications protocol is DICOM and the data comprises DICOM objects. However, the invention has application with any digital image communications standard or protocol.

Other aspects of the invention are disclosed and claimed below.

DETAILED DESCRIPTION

A DICOM network may comprise scanners of different modalities, a worklist broker (for interfacing an RIS or HIS to a DICOM network), storage devices, and printing devices, all connected to a local area network (LAN). Each DICOM-compatible scanner has the built-in capability to communicate with any one or more remote devices in conformance with the DICOM requirements. As used herein, the term "storage device" includes, but is not limited to, a picture archiving and communications system (PACS) having a viewing station.

Figure 1:
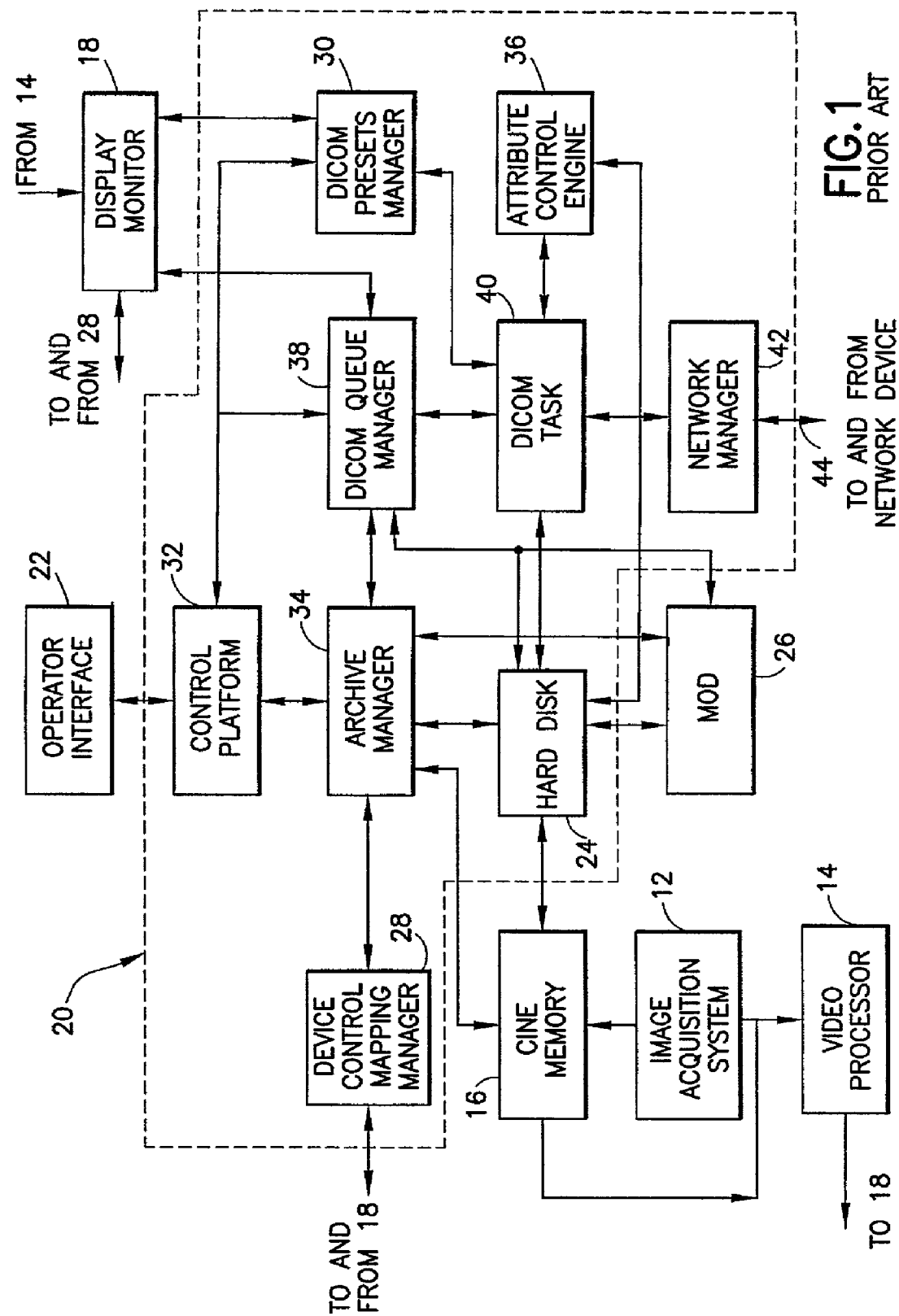
FIG. 1 is a block diagram representing a known imaging system that is programmed with DICOM capability.

For the purpose of illustration, portions of a known scanner, namely, a computerized ultrasound imaging system, are represented in FIG. 1. This scanner is programmed to communicate with remote devices over a network in conformance with the DICOM standard. An image acquisition subsystem of known construction acquires images from a patient. During image acquisition, each frame of imaging data is mapped into a gray-scale and/or color imaging format by a video processor 14. The video frame is then displayed on a display monitor 18. System control is centered in a host computer 20, which accepts operator inputs through an operator interface 22 and in turn controls the various subsystems. The operator interface comprises a keyboard, a trackball, a multiplicity of pushbuttons, and other input devices such as sliding and rotary knobs. During imaging, a long sequence of the most recent images can be stored and continuously updated automatically in a cine memory 16. The image loop stored in cine memory 16 can be reviewed via trackball control, and a section of the image loop can be selected for storage on a hard disk 24.

In response to a request from the operator to archive a frozen image, the control platform 32 sends an "Image Store" instruction to the archive manager 34. In response to the "Image Store" instruction, the archive manager retrieves the frozen image from cine memory 16 and stores it either on the hard disk 24 or on the MOD 26, depending on the system operator's selection.

Again referring to FIG. 1, it should be appreciated that all blocks residing inside the host computer 20, with the exception of the hard disk 24, are preferably, but not necessarily, implemented as software. In the system depicted in FIG. 1, commands inputted via the operator interface 22 are detected and processed by the control platform 32. In return, the control platform will provide signals to the operator interface that activate various visual indicators on the operator interface to indicate the status of various functions. In response to manipulation of the appropriate key or set of keys by the operator, the DICOM presets manager 30 will display a "Device Configuration" menu on the display monitor 18 that allows the system operator to enter configuration data for each destination remote device via the operator interface.

The scanner shown in FIG. 1 is designed to communicate with a configured remote device only if that device has been "activated". Activation causes the DICOM presets manager 30 to configure one of a multiplicity of DICOM tasks 40 in accordance with configuration data entered into the system for the associated remote device. That particular DICOM task will thereafter remain configured for that type of remote device until reconfigured for a different device. Other DICOM tasks are configured for other remote devices.

The scanner may be equipped with a plurality of Print/Store buttons on the operator interface 22. The device control mapping manager 28 constructs a mapping of DICOM tasks (configured for respective remote devices) to Print/Store buttons and provides that mapping to the archive manager 34. When the archive manager later receives a posting from the control platform 32 that a particular Print/Store button has been pressed, the archive manager 34 will refer to the device control mapping and determine the DICOM tasks 40 associated with the pressed button. The archive manager 34 then advises the DICOM queue manager 38 which DICOM tasks 40 need to construct objects incorporating the selected image frame. The DICOM queue manager 38 then copies that image file once for each task.

Thus, the system operator may request that a frozen image be sent to an activated remote device for printing or storage by pressing the appropriate Print/Store button. In response to a request from the operator to transfer a frozen image to a remote device, the control platform 32 sends an "Image Send" instruction to the archive manager 34. The archive manager 34 retrieves the frozen image from the cine memory 16 and stores it in a file on the hard disk 24. The file includes the image pixel data as well as certain attribute data, such as patient name, patient ID, gray-scale or color image, number of rows and columns of pixels, etc. Then the archive manager 34 notifies the DICOM queue manager 38 of the image to be transferred and the destination remote device that image (and subsequent images of the same job) will go to. Next the queue manager 38 copies the image to another location on the hard disk and gives that copied image a new file name.

In accordance with the DICOM standard, each DICOM task 40 is designed to convert an image file, comprising image frame data and attribute data, into a DICOM-formatted object, also comprising image frame and attribute data. That DICOM object must conform not only to the DICOM standards, but also to the attribute requirements of the remote device destined to receive that DICOM object. For this purpose, in the exemplary scanner shown in FIG. 1, each DICOM task 40 has a respective Attribute Control File associated therewith. Each DICOM task 40 constructs DICOM objects by associating attribute names and values with attribute tags identified in an associated Attribute Control File as being compatible with the destination remote device. An Attribute Control Engine 36 controls which attributes to include and which attribute names and values to associate with which attribute tags in the DICOM objects constructed by each DICOM task 40. When the system is powered up, the Attribute Control Engine 36 reads the Attribute Control Files from the hard disk 24 and writes them into system memory. These Attribute Control Files are kept in system memory for the duration of the power cycle. Each Attribute Control File comprises many lines for setting up the DICOM attributes. One line is needed to set up one DICOM attribute. The format of each line is as follows: [Module Name][Tag Number][Sequence Number] [Format String]The module name specifies the DICOM module that the attribute on that line belongs to. The module name is a defined term. The tag number specifies a particular attribute included in that module. Some DICOM attributes have the sequence of the subset of some DICOM attributes. The sequence number specifies the sequence that the attribute belongs to. The format string specifies how the data value of the attribute should be created.

Referring still to FIG. 1, each DICOM task 40 sends its DICOM object in proper format to the corresponding destination remote device via the network manager 42 and the port 44. The DICOM tasks run concurrently and independently of each other in accordance with conventional multi-tasking principles. Jobs which are waiting to be converted into DICOM objects by a DICOM task are queued. The queue is managed by the DICOM queue manager 38. Once the association is open and assuming that a channel on the network is available (i.e., the network is not busy), the image is sent from the scanner onto the network via network manager 42 and port 44. If the destination remote device sends back a message that the image transfer was successful, then the DICOM task 40 notifies the queue manager 38. The queue manager then removes the entry for the successfully transferred image from the queue and deletes that image file from the hard disk 24.

Figure 2:
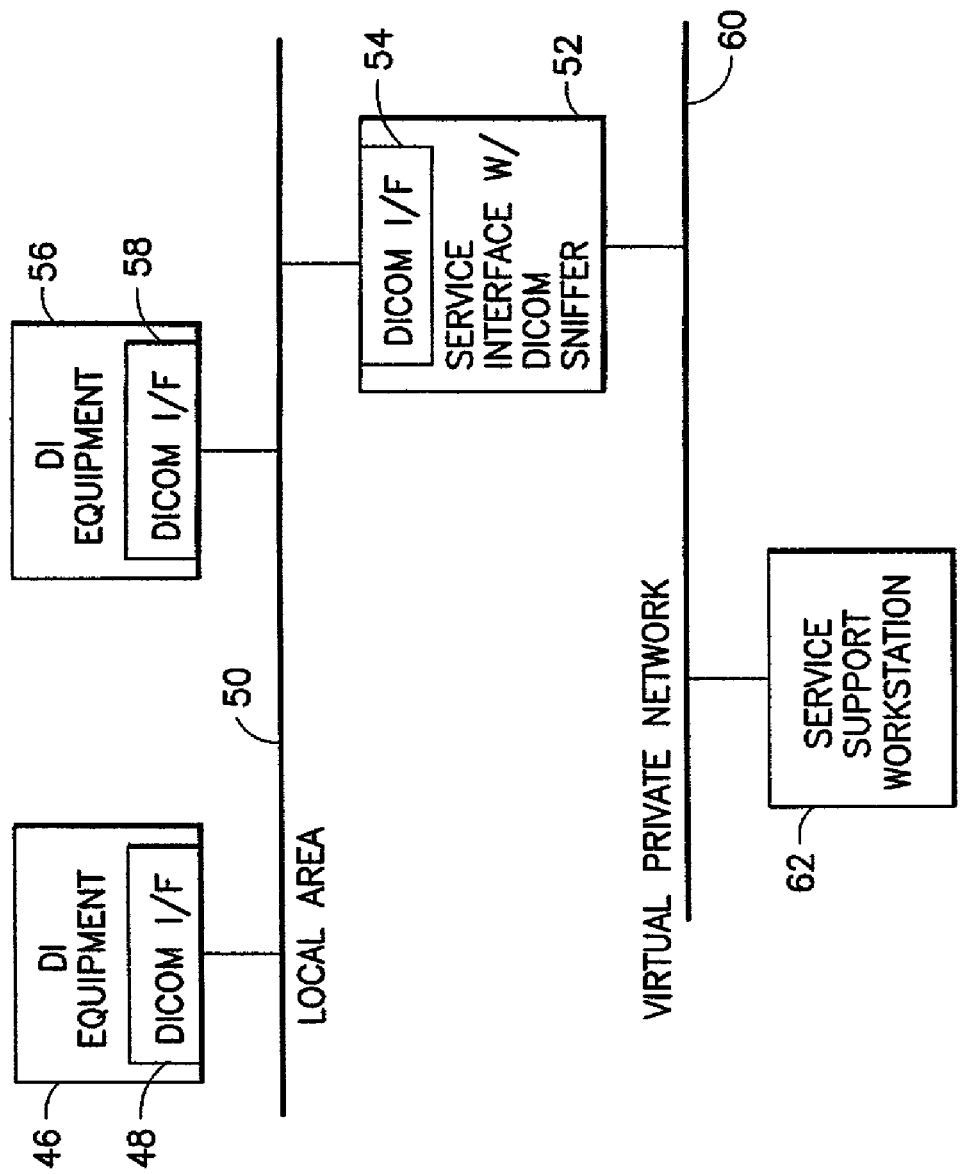
FIG. 2 is a block diagram representing a portion of a network in accordance with the preferred embodiment of the invention.

As previously discussed, a local area network (LAN) may have multiple DICOM-compatible diagnostic imaging equipment connected thereto, including, scanners, storage devices, printers, etc. For the purpose of disclosing the preferred embodiment of the present invention, FIG. 2 shows only two diagnostic imaging systems 46 and 56, each having a respective DICOM interface 48 and 58. Such a DICOM interface converts files into objects formatted in accordance with DICOM standards. (An exemplary DICOM interface for use in a scanner was described in detail with reference to FIG. 1.) Assuming that diagnostic imaging equipment 46 is a scanner and diagnostic imaging equipment 56 is a storage device, it is possible to send images in DICOM format from the scanner to the storage device via an LAN 50. Each DICOM data communication comprises a header that includes the address of the transmitting device and the address of the destination receiving device. The transmitting device sends the DICOM data communication onto the local area network; the receiving device recognizes its own address in the header of the DICOM data communication and then grabs the DICOM data communication off of the network.

In particular, a scanner can be configured to communicate with a DICOM-compatible computerized data capture device 52 connected to LAN 50. The data capture device 52 has a DICOM interface 54 that enables it to send and receive DICOM objects to and from the LAN 50. In this case, the data capture device can capture from the LAN any objects addressed to the data capture device.

In accordance with a preferred method of servicing a malfunctioning scanner, the scanner user can freeze a troubled image, i.e., an image of poor quality, and then request that the troubled image be sent to the data capture device by pressing the appropriate Print/Store button on the operator console. The troubled image, in DICOM format, is received and stored by the data capture device 52. The data capture device is in turn programmed to notify, e.g., via a virtual private network (VPN) 60, a service support workstation 62 located at a central service facility that a troubled image has been received from a particular scanner. Later the troubled image is sent via the VPN 60 to the service support workstation 62, where a service support engineer can view the troubled image and try to diagnose the image quality problem afflicting the malfunctioning scanner. The service support engineer can then take appropriate steps to instruct the scanner operator, repair the scanner or otherwise improve the image quality.

In addition, in accordance with a further preferred embodiment of the invention, the data capture device 52 can be programmed with data capture software that allows it to grab DICOM data communications originating from a specific scanner off of the network 50, even though the communications are not addressed to the data capture device. For example, a scanner user who is dissatisfied with the image quality on the scanner may contact a central service facility, e.g., by e-mail or by telephone. Upon learning the identity and location of the possibly malfunctioning scanner, a service support engineer at the service center can then send an instruction to the data device 52 via the virtual private network 60, instructing the data capture device to monitor the network traffic and capture DICOM communications originated from the malfunctioning scanner. The data capture device 52 preferably has a service interface for receiving instructions from a service support workstation 62 (e.g., a personal computer programmed with diagnostic software) at the central service facility. The instruction preferably includes the address (or other identifier contained in the DICOM communication) of the malfunctioning scanner. In accordance with the preferred embodiment, the data capture device 52 uses "sniffing" software to detect any DICOM communications on the LAN having a header that identifies the malfunctioning scanner as the addresser. The data capture device captures the transmitted DICOM files and later sends them to the central service facility for diagnosis of the image quality problem.

In accordance with an alternative method encompassed by the invention, the operator of the service support workstation may initiate monitoring of the traffic on LAN 50 by the data capture device 52 as part of a repair or service follow-up procedure. This allows a service provider to remotely monitor image quality on a scanner after the scanner has been serviced or repaired. The data capture device 52 can be instructed to capture all images on LAN 50 from a specific scanner (e.g., 46 or 56) for a predetermined period of time to ensure that the repair or service was performed properly.

In accordance with the preferred embodiment of the invention, a data capture device 52 captures troubled images off of a local area network 50 and then sends those troubled images for diagnosis to a central service facility via a virtual private network. Preferably, the virtual private network software is installed as part of the service center's firewall server. A typical virtual private network is a private data network that makes use of the public telecommunication infrastructure, maintaining privacy through the use of a tunneling protocol and security and security procedures. Using a virtual private network involves encrypting data before sending it through the public network and decrypting it at the receiving end. The data capture device is programmed with DICOM data capture software that captures DICOM image files from a specific scanner in response to an instruction from the service support workstation and later transmits those captured image files to the service support workstation 62. As used herein, the term "data capture software" incorporates so-called "sniffing software", which provides the service engineer or other user with a capability to detecting tag/value pairs contained in DICOM communications. For example, the "sniffing software" can detect DICOM objects on the LAN that originated from a particular scanner by detecting a unique identifier or address contained in the header of the DICOM object. The "sniffing software" can then collect and store all of the DICOM objects from the specified source. This data is stored in the data capture device 52 and forwarded to the central service facility either automatically or in response to a request for data.

In accordance with one preferred embodiment, the data capture device 52 is a computer programmed to collect data automatically in response to data collection requests received via the virtual private network 60. Alternatively, the data capture device may have a user interface, by means of which a service technician can input a data collection instruction. Once the data has been collected, the service technician can transmit the collected data to the service center via the virtual private network.

The capability to collect DICOM objects on a network allows a service vendor to service diagnostic imaging equipment manufactured by different OEMs. For example, images can be gathered from any scanner on an LAN and sent via a service support workstation at a central service facility for diagnosis of system performance problems. This capability can be extended to a multiplicity of medical devices that support an industry-recognized communications protocol, such as HL7, Unity and the like.

In accordance with another preferred embodiment, DICOM data capture software (including "sniffing software") can be downloaded from a secure web server via a wide area network to a computerized device, e.g., a workstation or a scanner, located on a local area network. Once the data capture software is installed on the computerized device, that computerized device can then be used, in the same way as the data capture device previously described, to capture data originating from a specific device on the local area network.

Figure 3:
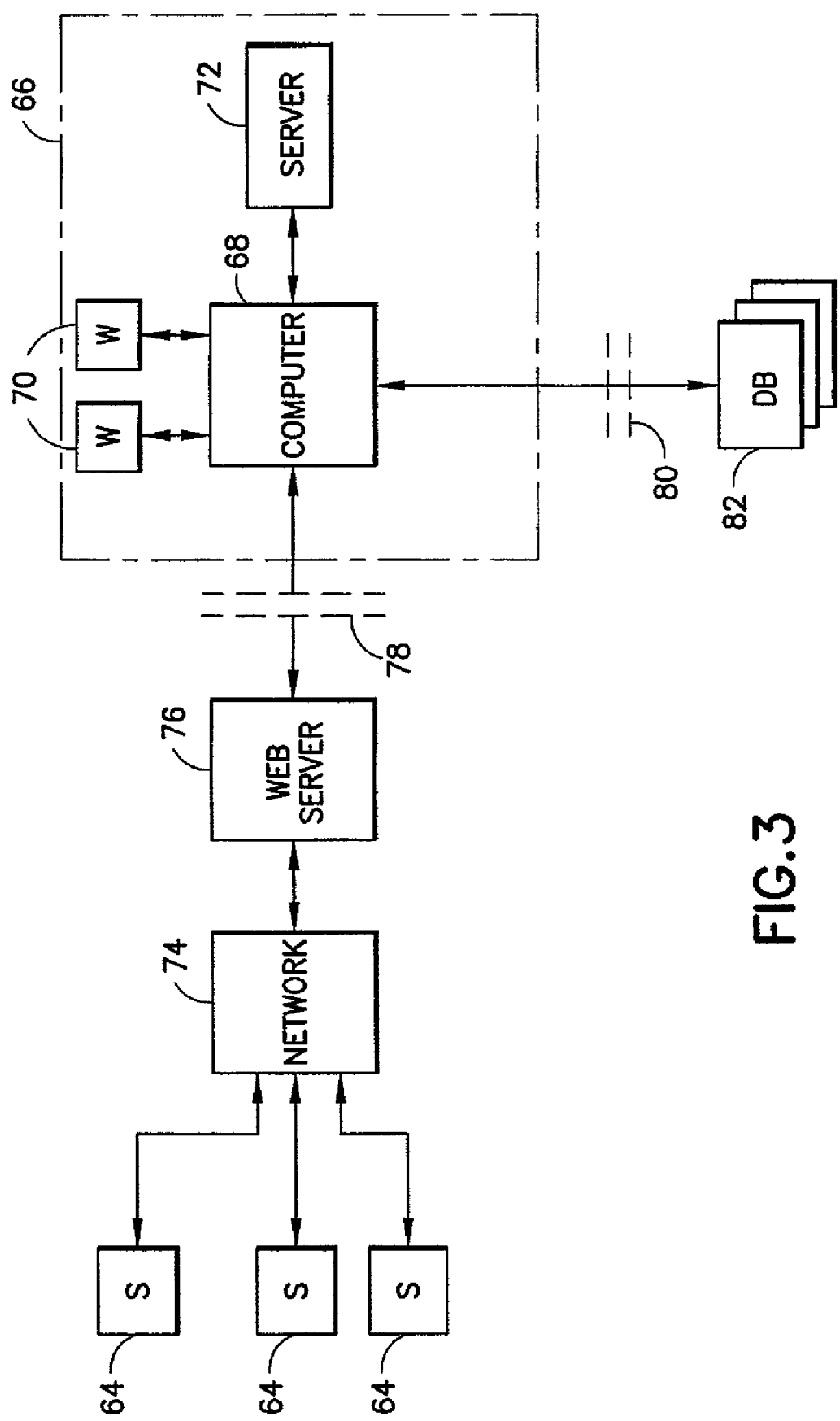
FIG. 3 is a block diagram representing a service network linked to a local area network via a web server in accordance with another preferred embodiment of the invention.

FIG. 3 is a diagrammatical representation of a number of diagnostic systems or scanners 64 coupled to a central service facility 66 via a remote data exchange network. In the embodiment illustrated in FIG. 3, scanners 64 may be of the same or different modalities and may be manufactured by different OEMs. Each scanner includes interactive communications hardware and software for communicating over a network represented generally by reference numeral 74. Network 74 may include an intranet, internet or other network, such as the Internet. In such cases, the scanners are preferably provided with network software, such as a graphical user interface and browser permitting operations personnel at a facility to send and receive messages to and from the central service facility. The network 74 permits the scanners to be coupled to a web server 76 which manages communications and data traffic between the central service facility and the scanners on the network.

The web server 76 may transmit and receive data to and from the scanners 64 via the network 74, and to and from the central service facility 66 through a firewall 78, particularly with a Point-to-Point Protocol (PPP). Firewall 78 may include any of various known security devices for preventing access to central service facility 66 except by recognized subscribers and other users. Central service facility 66 includes one or more central computers 68 which coordinate data exchange between the scanners 64 and service support workstations 70 at the central service facility. Workstations 70 may, in turn, be staffed by service personnel. Computer 68 may also be coupled for data exchange with one or more servers 72 at the central service facility. Moreover, computer 68 or other devices at the central service facility 66 may be coupled or configured to be coupled to other internal or external networks, such as for exchanging data with database 82 through an additional firewall 80. In the presently preferred configuration, database 82 may be local to or remote from the central service facility 66, and may contain data relating to the service history of particular scanners, families of scanners, and the like. Such data is compiled over time by transmission from computer 68, and is subsequently accessible by computer 68.

In accordance with the preferred embodiment depicted in FIG. 3, a service customer or a field engineer may download DICOM data capture software from the web server 76 to any one of the scanners 64 or to some other computerized device, e.g., a workstation, that can connect to network 74. The device loaded with DICOM data capture software can then be employed to perform data collection (as previously described with reference to FIG. 2) on a local area network to which the device is connected. (The respective local area networks for each scanner 64 are not depicted in FIG. 3.) That DICOM data capture software preferably includes not only sniffing software for collecting DICOM object originating from a specific scanner on the local area network, but also software for automatically transmitting the collected data to the web server 76 (and then on to the central service facility 66) in response to a data collection request or instruction sent via the web server 76 and network 74 from a service support workstation 70 to the scanner 64. In the case of DICOM files containing troubled images, the service support engineer at a workstation 70 will diagnose any image quality problems and take appropriate action based on the diagnostic results.

It is also contemplated that the DICOM data capture software may be downloaded from the web server to a scanner or other computerized device only by subscribing customers for which a conforming service contract or agreement has been completed or by an authorized field service engineer. In accordance with a preferred embodiment, a customer or field engineer must send an authorization code from the scanner 64 or other computerized device to the web server 76. The data capture software is downloaded from the web server 76 to the scanner 64 or other computerized device only if the inputted authorization code is valid. The web server may have a database of valid authorization codes stored in memory.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A method of remotely servicing a scanner from a central service facility, comprising the steps of:

monitoring traffic passing through a location on a local area network, said traffic comprising files or objects of digital image data that conform to a communications protocol in accordance with which each file or object has a header comprising an origination address that is the address of the respective device that transmitted the file or object onto said local area network and a destination address that is the address of the particular device destined to receive that file or object from said local area network, said monitoring step being performed by a computerized device that is connected to said location on said local area network and has an address different than the destination address;

transmitting an instruction signal from a central service facility to said computerized device via a network other than said local area network, said instruction containing the address of a specified scanner that is connected to said local area network, wherein said computerized device captures any file or object passing through said location on said local area network that has a header with an address identifying said specified scanner as the transmitting device, while not capturing any file or object passing through said location that has a header with an address identifying a transmitting device different than said specified scanner, said captured file or object comprising at least one image frame;

sending said captured file or object from said computerized device to said central service facility via said other network; and displaying said image frame at said central service facility.

2. The method as recited in claim 1, further comprising the step of diagnosing an image quality problem of said specified scanner that is visible in said displayed image frame.

3. The method as recited in claim 1, wherein said other network is a virtual private network.

4. The method as recited in claim 1, further comprising the step of downloading programming to said computerized device via a wide area network, said programming enabling said computerized device to perform said monitoring, capturing and sending steps.

5. The method as recited in claim 4, further comprising the steps of sending an authorization code from said computerized device to a server via said wide area network, and downloading said programming from said server to said computerized device only if said authorization code is valid.

6. The method as recited in claim 1, wherein said communications protocol is DICOM.

7. A system comprising:
a local area network;
a receiving device connected to said local area network;
a scanner connected to said local area network and having a capability of sending to said receiving device, via said local area network, image files formatted in accordance with a communications protocol, each image file incorporating at least one image frame;
a first computerized device at a central service facility;
a second computerized device connected to said local area network and programmed with data capture software to capture an image file on said local area network that originated from said scanner, but has a destination address that identifies said receiving device, in response to said scanner being specified as a target, and to not capture any image file on said local area network that originated from any scanner not specified as a target; and
a communications channel for connecting said first computerized device to said second computerized device, wherein said scanner is specified as a target by transmission of an instruction from said first computerized device to said second computerized device via said communications channel.

8. The system as recited in claim 7, wherein said data capture software comprises programming for sending said captured image file to said central service facility via said communications channel.

9. The system as recited in claim 7, wherein said communications channel is part of a virtual private network.

10. The system as recited in claim 7, wherein said communications protocol is DICOM.

11. The system as recited in claim 7, further comprising a server programmed to send said data capture software to said second computerized device via said communications channel.

12. The system as recited in claim 11, wherein said server is programmed to send said data capture software to said computerized device only in response to receipt of a valid authorization code from said computerized device.

13. A method of remotely servicing any one of a multiplicity of scanners connected to a local area network from a central service facility, comprising the steps of:
specifying one of said scanners to a computerized device connected to a location on said local area network;
monitoring traffic at said location on said local area network for the presence of any DICOM object originating from said specified scanner, said DICOM object being addressed to a receiving device connected to said local area network and comprising at least one image frame acquired by said specified scanner;
capturing said DICOM object;
sending said captured DICOM object to a central service facility via a network other than said local area network; and
diagnosing a problem associated with said specified scanner using said captured DICOM object received at said central service facility,
wherein said monitoring, capturing and sending steps are performed by said computerized device, said computerized device having an address different than the address of said receiving device.

14. The method as recited in claim 13, wherein said captured DICOM object is sent from said computerized device to said central service facility via a virtual private network.

15. The method as recited in claim 13, wherein said scanner is specified in a communication sent from said central service facility to said computerized device.

* * * * *